United States Patent [19]

Hayes et al.

[11] Patent Number: 5,167,662

[45] Date of Patent: Dec. 1, 1992

[54] TEMPORARY CLAMP AND INSERTER FOR A POSTERIOR MIDLINE SPINAL CLAMP

[75] Inventors: S. Kyle Hayes; Antony J. Lozier, both of Warsaw, Ind.

[73] Assignee: Zimmer, Inc., Warsaw, Ind.

[21] Appl. No.: 825,344

[22] Filed: Jan. 24, 1992

[51] Int. Cl.⁵ .................. A61B 17/56; A61B 17/08
[52] U.S. Cl. ........................................ 606/61; 606/151
[58] Field of Search .................. 606/61, 54, 59, 105, 606/151; 623/17; 403/290, 342, 365, 385

[56] References Cited

U.S. PATENT DOCUMENTS

| | | | |
|---|---|---|---|
| 251,825 | 1/1882 | Bruhl | 119/154 |
| 1,359,164 | 11/1920 | Lo Giudice | 606/205 |
| 1,832,879 | 11/1931 | Buskin | 606/208 |
| 2,507,710 | 5/1950 | Grosso | 606/205 |
| 3,999,555 | 12/1976 | Person | 128/785 |
| 4,050,464 | 9/1977 | Hall | 606/61 |
| 4,411,259 | 10/1983 | Drummond | 606/61 |
| 4,428,374 | 1/1984 | Auburn | 606/174 |
| 4,445,513 | 5/1984 | Ulrich | 606/61 |
| 4,448,191 | 5/1984 | Rodnyansky | 606/61 |
| 4,567,884 | 2/1986 | Edwards | 606/61 |
| 4,611,582 | 9/1986 | Duff | 606/61 |
| 4,648,401 | 3/1987 | Mattson | 606/174 |
| 4,856,518 | 8/1989 | McFadden | 606/151 |
| 4,896,661 | 1/1990 | Bogert et al. | 606/86 |
| 4,898,161 | 2/1990 | Grundei | 606/105 |
| 5,000,165 | 3/1991 | Watanabe | 606/61 |
| 5,000,166 | 3/1991 | Karpf | 606/61 |
| 5,007,909 | 4/1991 | Rogozinski | 606/61 |
| 5,074,864 | 12/1991 | Cozad | 606/54 |

Primary Examiner—Michael A. Brown
Attorney, Agent, or Firm—Todd A. Dawson

[57] ABSTRACT

The invention provides a temporary clamp for connection to the midline clamp which holds the midline clamp in engagement about the lamina and is small enough to be substantially out of the way of the surgeon in use. The temporary clamp is removably connected to the midline clamp by a pair of screws. The temporary clamp is releasably connected to a clamp inserter such that after the midline clamp and temporary clamp is connected to the vertebra, the clamp inserted may be removed and used to connect subsequent temporary clamps. Therefore, since the clamp inserter may be removed from the surgical site without releasing the midline clamp, the surgeon may connect a plurality of the midline clamps with temporary clamps attached without significantly obstructing the surgical site.

5 Claims, 5 Drawing Sheets

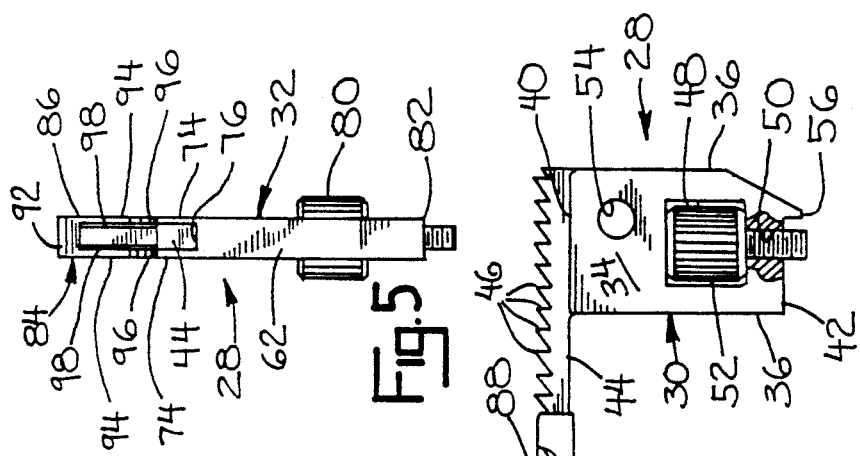
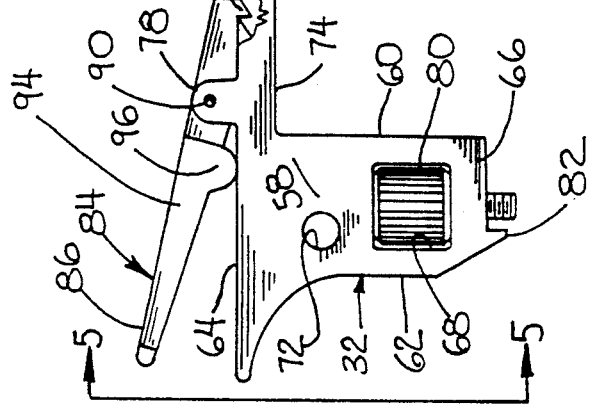
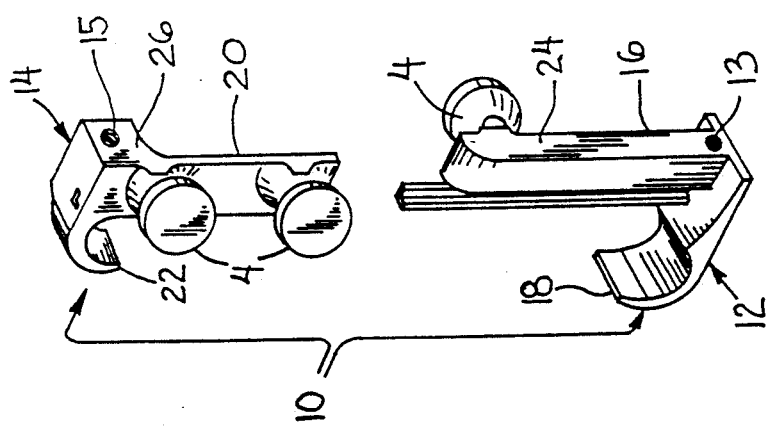
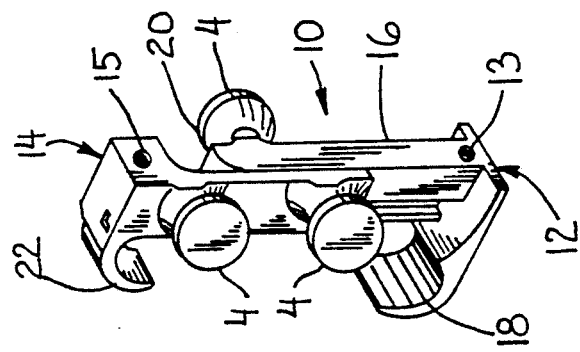

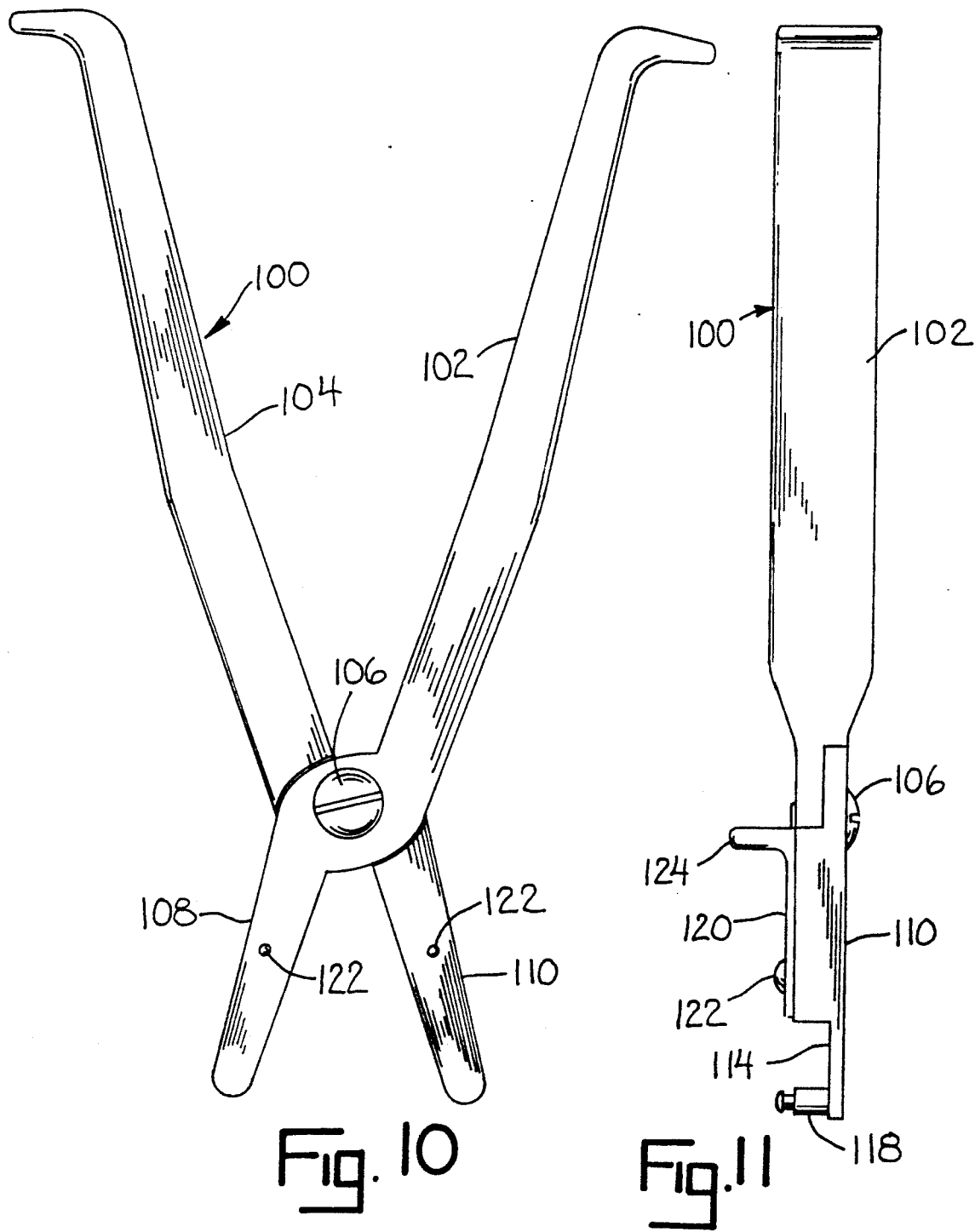

TEMPORARY CLAMP AND INSERTER FOR A POSTERIOR MIDLINE SPINAL CLAMP

FIELD OF THE INVENTION

This invention relates to a temporary clamp for a midline spinal clamp and to a temporary clamp inserter.

BACKGROUND OF THE INVENTION

To correct a spinal deformity, a pair of rods may be connected to the spinal column of a patient by a series of spinal hooks. Distraction or contraction is applied to the rods between the hooks to straighten or support the spinal column of the patient. One form of spinal hook is referred to as midline clamp and includes a pair of hooks in sliding engagement with one another. A midline clamp is illustrated in U.S. patent application Ser. No. 07/287,245 filed Dec. 12, 1988 in the name of Cozad el al., incorporated herein by reference.

During the surgical procedure it is not uncommon for the surgeon to loosely position a plurality of midline clamps along the spine of the patient prior to actually connecting the rods to the clamps. To connect the midline clamp to the lamina on the posterior side of the spine, a clamp inserter (resembling a pair of pliers with a special jaw) directly engages each of the parts of the midline clamp to compress the midline clamp about the lamina. As mentioned, the midline clamps are formed from two slidable engaging hooks. Therefore, to maintain the clamps in position about the lamina until the rods are securely connected, the clamp inserter must remain connected to the midline clamp. It would not be uncommon for a corrective spinal procedure to require a plurality of midline clamps each being connected and held in place by the clamp inserters in the manner described above. Therefore, using the current midline clamps and clamp inserter, each midline clamp and its connected inserter must remain attached to the spine until the spinal rods are connected and yet must be positioned out of the way of the surgeon. Typically, this would means that the clamp inserter must be held by a surgical assistant or laid down on the patient adjacent the surgical site. For example, if five midline clamps were to be connected, then there would be five clamp inserters along the surgical site.

SUMMARY OF THE INVENTION

The invention provides a temporary clamp for connection to the midline clamp which holds the midline clamp in engagement about the lamina and is small enough to be substantially out of the way of the surgeon in use. The temporary clamp is removably connected to the midline clamp by a pair of screws. The temporary clamp is releasably connected to a clamp inserter such that after the midline clamp and temporary clamp is connected to the vertebra, the clamp inserted may be removed and used to connect subsequent temporary clamps. Therefore, since the clamp inserter may be removed from the surgical site without releasing the midline clamp, the surgeon may connect a plurality of the midline clamps with temporary clamps attached without significantly obstructing the surgical site.

Accordingly, it is an object of this invention to provide for a novel temporary clamp for a midline spinal clamp.

Another object of the invention is to provide a temporary clamp for a midline spinal clamp which directly connects to the midline clamp.

Another object of this invention is to provide for a novel temporary clamp inserter.

Yet another object of the invention is to provide for a novel midline clamp adapted for connection to a temporary clamp.

Still other objects of the invention will become apparent upon a reading of the following description taken with the following drawings.

BRIEF DESCRIPTION OF THE DRAWINGS

FIG. 2 is a perspective view of a midline clamp of the invention.

FIG. 3 is an exploded perspective view of the midline clamp of FIG. 2.

FIG. 4 is a side elevational view of the connector for a midline clamp with portions cutaway for illustrative purposes.

FIG. 5 is an elevational view taken along line 5—5 of FIG. 4.

FIG. 10 is a rear side elevational view of the inserter handle.

FIG. 11 is a right side elevational view of the clamp handle.

DESCRIPTION OF THE PREFERRED EMBODIMENT

The preferred embodiments herein disclosed are not intended to be exhaustive or to limit the invention to the precise forms disclosed. Rather, they are chosen and described to enable others skilled in the art to utilize its teachings.

Figure 1:
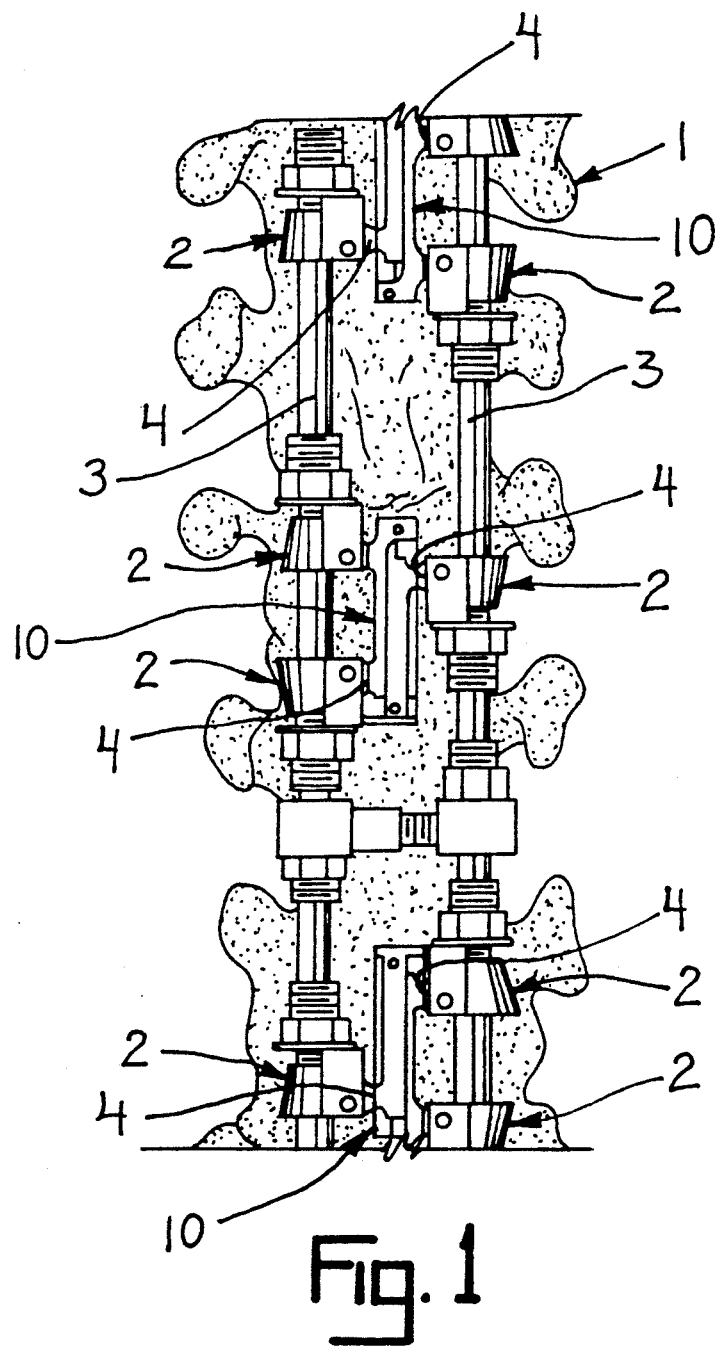
FIG. 1 is a fragmented elevation view of a spinal column having a pair of spinal rods connected to the vertebrae by a series of midline clamps and brackets.

FIG. 1 illustrates a spinal column 1 having a pair of longitudinal rods 3 connected to the spinal column by a plurality of midline clamps 10. Each midline clamp 10 is attached to the rod by locking sleeve assemblies 2. The locking sleeve assemblies engage the rod sections in a known manner and are shiftably connected to the midline clamps by the accommodation of studs 4 within a slot opening on the locking sleeve assembly. A more detailed description of the structure and function of the locking sleeve assemblies may be had by reference to the incorporated patent.

The midline clamp 10 as illustrated in the figures includes an inferior clamp half 12 and a superior clamp half 14. The inferior clamp half 12 includes a body 16, a posterior and anterior side and a shoe or a hook-like 18 configuration. Similarly, superior clamp half 14 includes a body 20 and a shoe or hook-like 22 configuration extending from the anterior side of the first and second clamp halves. The body 16 of inferior shoe 12 is wider than the body 20 of superior shoe 14. The clamp halves 12, 14 are slidably connected to one another through a cooperating L-shaped rib and groove formed in the clamp halves (not shown). The inferior clamp half 12 has incorporated therewith a transverse outwardly extending stud 4 on an end of the body 16 as shown. The superior clamp half 14 includes two studs 4 extending from the body 20. As mentioned previously, studs 4 of clamp halves 12, 14 are accommodated within a slot in the locking sleeve assemblies 2 to connect the clamp to the spinal rods. Each clamp half 12, 14 includes a threaded blind bore 13, 15, respectively, formed in the posterior side and the shoe end of the body extending from the front faces 24, 26 of the clamp halves.

Temporary clamp 28 includes generally L-shaped halves 30, 32. Half 30 includes a body 34 having a front inside edge 36, a rear side edge 38, a top edge 40, and a bottom edge 42. An arm 44 extends from top edge 40 of body 34 and is generally perpendicular to the front edge 36. Arm 44 includes a plurality of teeth 46 along its length. Arm 44 is smaller in cross section than body 34. Body 34 further includes a squared opening 48 as illustrated. A bore 50 extends from bottom edge 42 and is in communication with opening 48. A screw 52 is carried within opening 48 and includes a threaded shaft which extends through bore 50. An opening 54 is formed through body 34 between squared opening 48 and top edge 40. An abutment 56 extends downwardly from bottom edge 42 of body 34.

Temporary clamp half 32 includes a body 58 having a front edge 60, a rear edge 62, a top edge 64, and a bottom edge 66. A squared opening 68 is formed through body 58. A throughbore (not shown) extends from bottom edge 66 into squared opening 68. A screw 80 is carried within squared opening 68 and includes a threaded shaft extending through the throughbore. An opening 72 is formed through the body 58 and is oriented between squared opening 68 and top edge 64. An abutment 82 extends downwardly from bottom edge 66 or body 58. A pair of arms 74 extend along top edge 64 and are generally perpendicular with front edge 60 and rear edge 62. Arms 74 are spaced apart to define a channel 76 therebetween extending along the top edge of body 58. Each arm 74 includes a protrusion 78. A ratchet arm 84 having a handle portion 86 a ratchet tooth 88, and a center portion that extends towards the tooth end and is pivotally connected to body 58 by a connecting pin 90 traversing the ratchet arm and seated within aligned openings of protrusions 78 of arms 74. A pair of longitudinal slots 98 are formed in the handle portion 86 of arm 84 and extend from a midpoint of the arm toward the handle end 92 terminating adjacent end 92. The slots define spring arms 94 for the handle portion. Each spring arm includes a fulcrum 96. Each fulcrum 96 connects an arm 74. Fulcrums 96 and spring arms 94 combine to bias handle end 92 away from arms 74.

Clamp inserted 100 includes a pair of cross linked handle parts 102, 104 pivotally connected to one another by a pin 106. Handle members 102, 104 include jaw portions 108, 110. Leaf springs 112 are connected to the handle part to bias the handle parts away from one another. Each jaw portion 108, 110 includes a recessed section 114 forming a shoulder 116. A pin 118 extends upwardly from the distal tip of the recessed portion. Pin 118 includes an annular groove which is aligned with the upper surface of the shoulder 116. A clip 120 is slidably connected to the jaw portion by a screw 122 and includes an open end for clamping about pin 118 at the annular grove. The clip includes a thumb tab 124 for access by the user to slide the clip between an extended position wherein the clip extends over the recessed area and engaged pin 118 and a retracted position wherein the clip is clear of the recessed area.

In use, the inferior and superior clamp halves are positioned in engagement with one another. Clamp halves 30, 32 are positioned such that arm 44 of clamp half 30 is between arms 74 of clamp half 32 with the ratchet tooth 88 engaging teeth 46. One clamp half (30, 32) is connected to inferior clamp half by tuning screw 52 or 80 into the blind bore 13. Similarly, the other clamp half (30, 32) is connected to the superior clamp half 14 in the same manner. As illustrated in the figures, abutments 56, 62, contact the ends of the superior/inferior clamp halves. With the temporary clamp halves 30, 32 connected to the inferior and superior clamp halves 12, 14, the inferior and superior clamp halves, carrying the temporary clamp halves, are slidable in a direction toward each other causing ratchet arm 84 to ratchet over teeth 46. However, handle 86 must be depressed to pivot the arm 84 for disengaging the ratchet tooth 88 from teeth 46 to permit the midline clamp parts from shifting away from one another.

Figure 6:
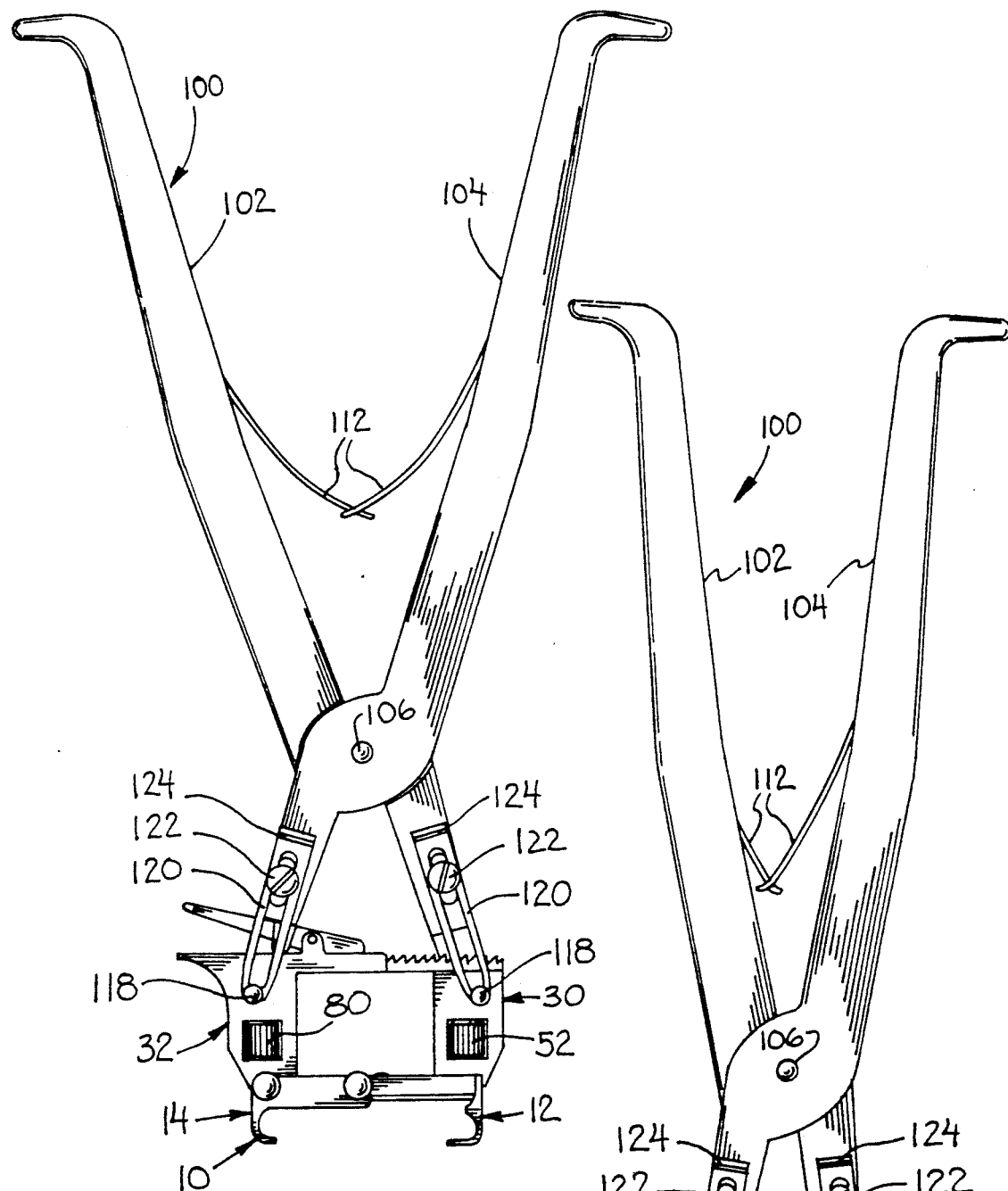
FIGS. 6–8 illustrate in series the procedure for connecting a midline clamp and connector to a vertebra and for releasing the inserter to leave the clamp and connector connected to the vertebra.
Figure 7:
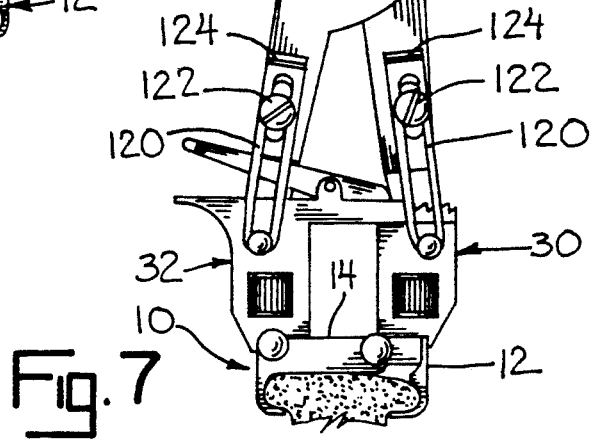
Figure 9:
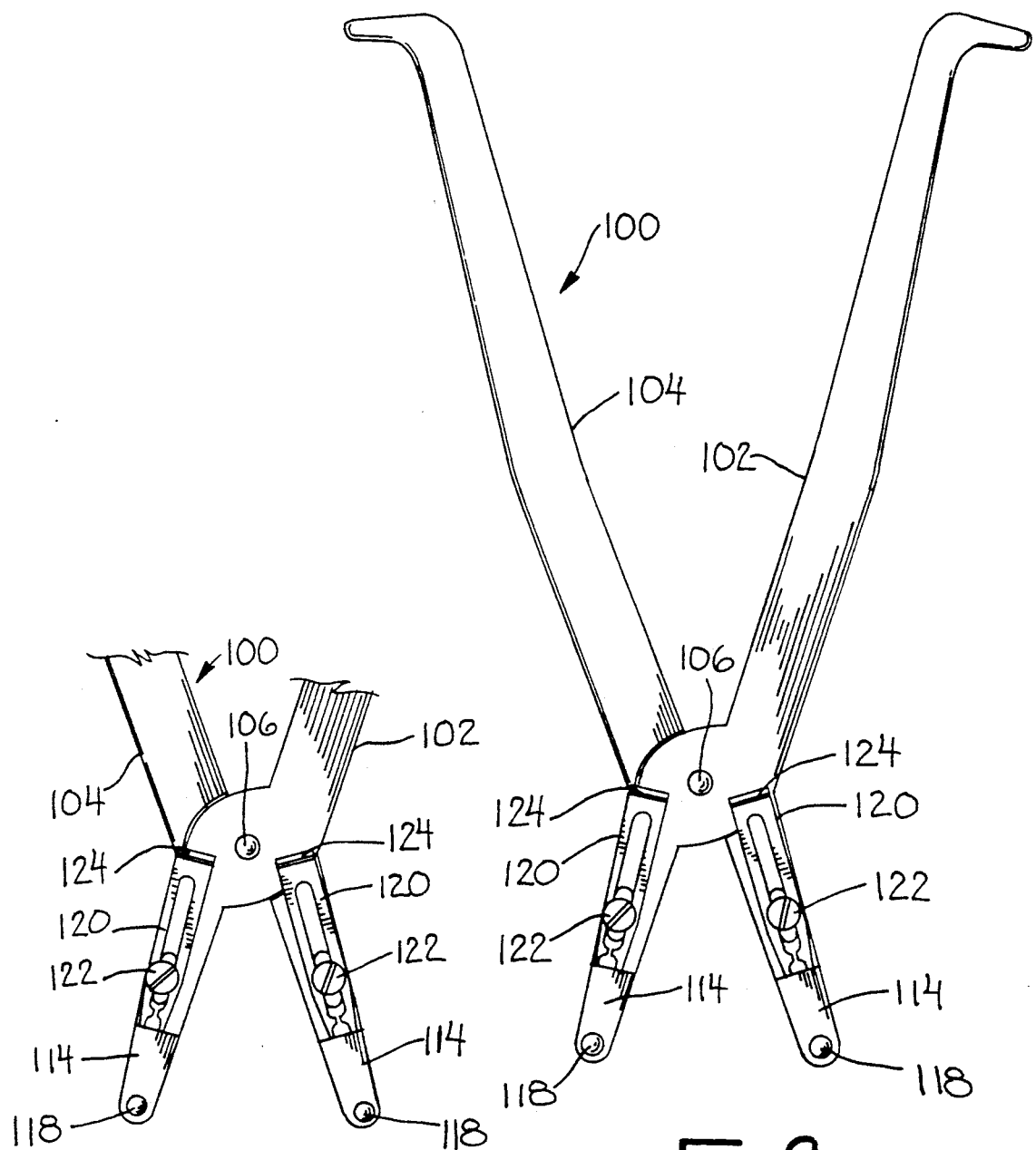
FIG. 9 is a front side elevational view of the inserter of the invention.

To connect the midline clamp 10, with temporary clamp 28 attached thereto, to the lamina of a vertebrae, clamp inserter 100 is connected to the temporary clamp in the following manner. As illustrated and described previously, each haw of the inserter includes a pin 118 extending transverse to the jaw. Pin 118 of each jaw 108, 110 is inserted through opening 54 and 72 of temporary clamp halves 30, 32. The temporary clamp halves seat against the recessed portions of the jaws. To secure, the temporary clamp 28 to the clamp inserter 100, clips 120 are slid into engagement with pins 118 with the temporary clamp halves retained therebetween (See FIGS. 6 and 7).

The surgeon next positions the midline clamp 10 about the lamina and squeezes the handles 86 of the inserter together causing the jaws to pivot toward each other and the spinal clamp and temporary clamp halves to compress together. The surgeon continues to position the midline clamp in clamping engagement with the vertebra. (See FIG. 7).

Figure 8:
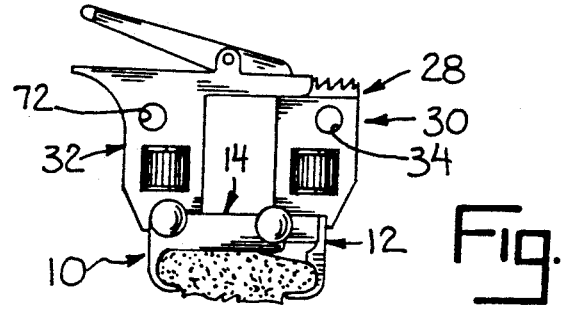

Clips 120 are shifted away from pins 118 and the inserter instrument pins are slid from openings 54 and 72 and the inserter instrument is removed. The ratchet engagement between ratchet tooth 88 and teeth 46 of the temporary clamp halves holds the temporary clamp halves and the midline clamp in clamping engagement with the lamina. (See FIG. 8).

After the locking sleeve assemblies 2 are connected to the midline clamp 10, or the clamp is secured to a spinal system by another means, the temporary clamp may be removed by turning screw 52 and 80 to rotate the screws out of bores 13 and 15.

It should be understood that during a surgical procedure to correct a spinal deformity, a number of the midline clamps may be required. Therefore, a like number of temporary clamps are required, but only one clamp inserter instrument 100 is required to sequentially position the clamps.

It should also be understood that the invention is not to be limited to the details above, but may be modified within the scope of the appended claims.

We claim:

1. A temporary clamp for connection to a midline spinal clamp to temporarily maintain the spinal clamp in clamping engagement with a vertebra, the spinal clamp including first and second halves each having a posterior side, a threaded blind bore being formed in each posterior side of the first and second spinal clamp halves, the temporary clamp comprising a first temporary clamp half having a body and an arm extending therefrom, a screw being carried by the first temporarily clamp half body for turning within the blind bore of the first spinal clamp half to connect the first temporary clamp half to the first spinal clamp half, a second temporary clamp half having a body and a pair of parallel arms extending therefrom, a screw being carried by the second temporary clamp half for turning within the blind bore of the second spinal clamp half to connect the second temporary clamp half to the second spinal clamp half, the arm of the first temporary clamp half being slidably received between the parallel arms of said second temporary clamp half, the first and second temporary clamp halves being shiftable together, and means carried by the temporary clamp halves for permitting the first and second temporary clamp halves to only shift towards one another when the means is in a first position, said means being shiftable to a second position to permit the temporary clamp halves to shift apart, wherein with the spinal clamp in clamping engagement with a vertebra and connected to the temporary clamp, and the means in its first position, the spinal clamp halves are prevented by the means from shifting away from one another to thereby maintain the clamping engagement wherein the means comprises a plurality of ratchet teeth carried by the arm of the first temporary clamp half, a ratchet arm having a tooth end and a handle end being carried by the parallel arms of the second temporary clamp half and pivotal between a first position wherein the tooth is between the parallel arms and a second position wherein the tooth is pivoted about said parallel arms, wherein when the means is in its first position the ratchet arm is in its first position and the tooth of the ratchet arm is engaging the teeth of the arm, with said means in its second position, the ratchet arm is in its second position and said tooth is disengaged with said ratchet teeth.

2. The temporary clamp of claim 1 wherein the ratchet arm includes a pair of parallel slots extending from the tooth end toward the handle end, the slots defining spring arms, each of the spring arms including a downwardly extending fulcrum contacting the parallel arms of the second temporary clamp half, a center portion of the ratchet arm extends toward the tooth end an is pivotally connected to the parallel arms, wherein the spring arms and fulcrums bias the ratchet arm toward its first position.

3. In combination, a midline spinal clamp, a temporary clamp and a temporary clamp inserter for positioning the midline clamp in clamping engagement about a portion of a vertebra and maintaining the clamping engagement until the temporary clamp is removed from the midline clamp, the midline clamp including first and second spinal clamp halves each having posterior and anterior sides, a threaded blind bore being formed in each posterior side of the first and second spinal clamp halves, a spine engaging hook extending from the anterior side of the first and second spinal clamp halves, the temporary clamp including a first temporary clamp half having a body with an arm extending therefrom, an opening is formed through the body of the first temporary clamp half for accommodating the temporary clamp inserter, a screw being carried by the first temporary clamp half body seated within the blind bore of the first spinal clamp half to connect the first temporary clamp half to the first spinal clamp half, a second temporary clamp half having a body and a pair of parallel arms extending therefrom, an opening formed through the body of the second temporary clamp half, a screw being carried by the second temporary clamp half seated within the blind bore of the second spinal clamp half to connect the second temporary clamp half to the second spinal clamp half, the arm of the first temporary clamp half being slidably received between the parallel arms of said second temporary clamp half, the first and second temporary clamp halves being shiftable together, and means carried by the temporary clamp halves for permitting the first and second temporary clamp halves to only shift towards one another when the means is in a first position, said means being shiftable to a second position to permit the temporary clamp halves to shift apart, the temporary clamp inserter including jaw members pivotally associated with one another, each jaw member including a pin for traversing the opening in each of the temporary clamp halves to connect the temporary clamp to the temporary clamp inserter, wherein with the inserter instrument, temporary clamp and midline clamp connected, the jaw members shifting toward each other cause the first and second halves of the temporary clamp and of the midline clamp to compress such that the spine engaging hooks clampingly engage a portion of the vertebra, wherein with the midline clamp is clamping engagement with a vertebra and connected to the temporary clamp and the means in its first position, the midline clamp halves are prevented by the means from shifting away from one another to thereby maintain the clamping engagement.

4. The combination of claim 3 wherein the means comprise a plurality of ratchet teeth carried by the arm of the first temporary clamp half, a ratchet arm having a tooth end and a handle end being carried by the parallel arms of the second temporary clamp half and pivotal between a first position wherein the tooth is between the parallel arms and a second position wherein the tooth is pivoted above said parallel arms, wherein when the means is in its first position, the ratchet arm is in its first position and the tooth of the ratchet arm is engaging the teeth of the arm, with said means in its second position, the ratchet arm is in its second position and said tooth is disengaged with said ratchet teeth.

5. The combination of claim 3 further including clips carried by the jaws of the inserter, the clips being shiftable between a retracted position spaced from the pins and an extended position in contact with the pin, wherein with the temporary clamp being carried by the clamp inserter instrument the pins are shifted from the first retracted position to the second extended position to lock the temporary clamp to the temporary clamp inserter.

* * * * *